United States Patent
Alibek et al.

(10) Patent No.: US 11,479,749 B2
(45) Date of Patent: *Oct. 25, 2022

(54) PRODUCTION AND CRYOPRESERVATION OF HIGH CONCENTRATION INOCULA

(71) Applicant: LOCUS IP COMPANY, LLC, Solon, OH (US)

(72) Inventors: Ken Alibek, Solon, OH (US); Sean Farmer, North Miami Beach, FL (US); Alibek Moldakozhayev, Solon, OH (US)

(73) Assignee: LOCUS IP COMPANY, LLC, Solon, OH (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/547,729

(22) Filed: Aug. 22, 2019

(65) Prior Publication Data

US 2019/0376021 A1    Dec. 12, 2019

Related U.S. Application Data

(63) Continuation-in-part of application No. PCT/US2018/026561, filed on Apr. 6, 2018.

(60) Provisional application No. 62/483,062, filed on Apr. 7, 2017.

(51) Int. Cl.
| | |
|---|---|
| *C12M 1/34* | (2006.01) |
| *C12N 1/04* | (2006.01) |
| *A01N 1/02* | (2006.01) |

(52) U.S. Cl.
CPC .............. *C12M 41/32* (2013.01); *A01N 1/02* (2013.01); *C12N 1/04* (2013.01)

(58) Field of Classification Search
CPC ....................................................... C12N 1/04
See application file for complete search history.

(56) References Cited

U.S. PATENT DOCUMENTS

| | | | |
|---|---|---|---|
| 4,332,904 A | 6/1982 | Kurane et al. | |
| 7,422,737 B1 * | 9/2008 | Nussinovitch | C12N 1/14 424/93.4 |
| 8,454,983 B2 | 6/2013 | DeChant et al. | |
| 2003/0228402 A1 | 12/2003 | Franklin et al. | |
| 2007/0074451 A1 * | 4/2007 | Pearce | A01N 63/20 47/57.6 |
| 2008/0138862 A1 | 6/2008 | Felby et al. | |
| 2009/0029879 A1 | 1/2009 | Soni et al. | |
| 2009/0280212 A1 | 11/2009 | Sugimoto et al. | |
| 2011/0044972 A1 | 2/2011 | Fieldhouse et al. | |
| 2012/0039853 A1 | 2/2012 | Corveleyn et al. | |
| 2013/0260450 A1 | 10/2013 | Fey et al. | |
| 2013/0324406 A1 | 12/2013 | Chisholm et al. | |
| 2013/0337108 A1 | 12/2013 | Van Hee | |
| 2014/0087173 A1 | 3/2014 | Boles et al. | |
| 2015/0044356 A1 | 2/2015 | Bootsma et al. | |
| 2015/0305347 A1 | 10/2015 | Wicks et al. | |
| 2016/0106117 A1 | 4/2016 | Gazenko | |
| 2016/0152525 A1 | 6/2016 | Chelle et al. | |

FOREIGN PATENT DOCUMENTS

| | | |
|---|---|---|
| CN | 102220386 A | 10/2011 |
| CN | 102533597 A | 7/2012 |
| CN | 103468622 A | 12/2013 |
| CN | 106135503 A | 11/2016 |
| EP | 2390345 A1 | 11/2011 |
| EP | 3029147 A1 | 6/2016 |
| WO | 9525163 A1 | 9/1995 |
| WO | 2014159309 A1 | 10/2014 |
| WO | 2015089183 A2 | 6/2015 |
| WO | 2018049182 A2 | 3/2018 |

OTHER PUBLICATIONS

Kearney, L. et al. 1990. Enhancing the viability of Lactobacillus plantarum inoculum by immobilizing the cells in calcium-alginate beads incorporating cryoprotectants. Applied and Environmental Microbiology, 56(10), pp. 3112-3116. (Year: 1990).*
Gehrt, A. et al. 1995. Effect of increasing inoculum sizes of pathogenic filamentous fungi on MICs of antifungal agents by broth microdilution method. Journal of Clinical Microbiology, 33(5), pp. 1302-1307. (Year: 1995).*
Smrdel, P. et al. 2008. The influence of selected parameters on the size and shape of alginate beads prepared by ionotropic gelation. Scientia Pharmaceutica, 76(1), pp. 77-90. (Year: 2008).*
Vedaraman N. et al. The effect of medium composition on the production of sophorolipids and the tensiometric properties by Starmerella bombicola MTCC 1910. Polish journal of chemical technology. 2010;12(2):9-13. (Year: 2010).*
Batabura, I. et al. 2012. Leydig cells encapsulation with alginate-chitosan: optimization of microcapsule formation. Journal of Encapsulation and Adsorption Sciences (Year: 2012).*
Bajaj, I. et al. 2014. Functional characterization of a Penicillium chrysogenum mutanase gene induced upon co-cultivation with Bacillus subtilis. BMC microbiology, 14(1), pp. 1-16. (Year: 2014).*
Patel, Y. et al. 2015. Biological Treatment of Textile Dyes by Agar-Agar Immobilized Consortium in a Packed Bed Reactor. Water Environment Research, 87(3), pp. 242-251. (Year: 2015).*
OPS Diagnostics (Author not listed. 2016. A guide to bacteria preservation: refrigeration, freezing, freeze drying. Company website) (Year: 2016).*
Sprouffske, K. et al. 2016. How archiving by freezing affects the genome-scale diversity of *Escherichia coli* populations. Genome biology and evolution, 8(5), pp. 1290-1298. (Year: 2016).*

(Continued)

*Primary Examiner* — Nghi V Nguyen
(74) *Attorney, Agent, or Firm* — Saliwanchik, Lloyd & Eisenschenk (57) ABSTRACT

The subject invention provides standardized, high concentration inocula in solid form for use as seed cultures in scaled-up cultivation. Further embodiments include methods of producing standardized inocula, as well as methods of preserving and storing the inocula for convenient use over extended periods of time.

13 Claims, 1 Drawing Sheet

(56) References Cited

OTHER PUBLICATIONS

Nelson, R. et al. 2017. Mixed carboxylic acid production by Megasphaera elsdenii from glucose and lignocellulosic hydrolysate. Fermentation, 3(1), p. 10. (Year: 2017).*

Das, N., et al., "Progress in the development of gelling agents for improved culturability of microorganisms." Frontiers in Microbiology, Jul. 2015, 6(698): 1-7.

* cited by examiner

PRODUCTION AND CRYOPRESERVATION OF HIGH CONCENTRATION INOCULA

CROSS-REFERENCE TO RELATED APPLICATION

This application is a continuation-in-part (CIP) application of International Application No. PCT/US2018/026561, filed Apr. 6, 2018; which claims the benefit of U.S. provisional application Ser. No. 62/483,062, filed Apr. 7, 2017, which is incorporated herein by reference in its entirety.

BACKGROUND OF THE INVENTION

Cultivation of microorganisms such as bacteria, yeast and fungi is important for the production of a wide variety of useful bio-preparations. Microorganisms play crucial roles in, for example, the food industry, pharmaceuticals, agriculture, mining, environmental remediation, and waste management.

Two principle forms of cultivation of microorganisms exist for producing bacteria, yeasts and fungi, which include submerged cultivation and surface cultivation. Both cultivation methods require a nutrient medium for the growth of the microorganisms. The nutrient medium, which can either be in a liquid or a solid form, typically includes a carbon source, a nitrogen source, salts and appropriate additional nutrients and microelements. The pH and oxygen levels are maintained at values suitable for a given microorganism.

Often, inoculum cultures, or inocula, are used to prepare a scaled population of microorganisms in a culture medium. To produce inocula, microbiology laboratories routinely use standardized reference cultures that can provide a predetermined quantity of microorganisms for use in, for example, a series of repeated experiments. Reference cultures are generally prepared by diluting a culture of microorganisms to obtain a fresh cell suspension that contains an estimated number of colony-forming units per milliliter (CFU/mL).

As a first step in inoculum development, inoculum is taken from a working stock culture or a reference culture to initiate growth in a suitable culture medium. For example, bacterial vegetative cells and spores are suspended, usually, in sterile tap water or saline, which can then be added to fermentation broth. Inoculum development is usually performed in a stepwise fashion to increase the volume of culture to the desired level. This stepwise process can lead to variability in yields and productivity, which in turn can lead to inefficient cultivation and substantial time spent preparing inocula.

Consistency in size and quality of inocula is an important aspect of inoculum production. Despite this fact, most inoculum development processes involve at least one highly variable transfer step from the initial reference culture medium to the final cultivation medium. Thus, at least some of the variability in the production process can be attributed to poorly controlled initial inoculation. Variability can also be caused by contamination, as each step in which inoculum culture is transferred from one vessel to another increases the risk that undesirable microorganisms will be introduced into the culture.

Additionally, the accuracy with which the number of CFU/mL can be determined often varies greatly due to the extrapolation of small measurement errors during dilution, as well as the biological variability of the sample. As such, using subsequently prepared, fresh reference cultures naturally increases the potential for false or invalid results, as it is difficult to consistently determine the number of CFU/mL for each single inoculum in a series of experiments. Furthermore, because of the multitude of stages of cultivation involved, there is a high probability for mutations to occur in the culture, leading to differences in the end product.

Currently, providing a plurality of inocula containing a relatively precise and consistent number of microorganisms with a reproducible amount of variation is a complex process. Further, the precision required during preparation can lead to increased costs and time required for such processes.

Thus, there is a need for inexpensive and straightforward methods for producing multiple consistent inocula from reference cultures that can be used for repeatable cultivation of microbe-based products.

SUMMARY OF THE INVENTION

The present invention provides methods for producing and preserving microorganisms that can be used in research labs and in microbe-based compositions used in industries such as oil and gas, agriculture, bioremediation, aquaculture, human and animal health and many others. Specifically, the subject invention provides methods and materials for efficient cultivation of inocula for producing microorganisms and microbial growth by-products.

In specific embodiments, the subject invention provides simple, reliable methods of producing large quantities of standardized, high concentration inocula in solid form. Advantageously, the methods allow for production of inocula that can be preserved and stored for an extended period of time, for example a period of months or even several years or more.

Additionally, the inocula are relatively inexpensive to produce, and can significantly decrease the amount of work, money and time that must be spent producing cultures for research and/or other uses. The method can help prevent the culture from developing mutations over time, thus enabling genetically consistent culture for research and production. The inocula can also be shaped and sized to enable a user to conveniently and accurately transfer a specified amount of inoculating material, such as a specific number of cells, propagules or microorganisms, from one container to another, using standard laboratory equipment. Furthermore, the present invention can simplify production and facilitate consistent repetition of cultivation procedures while also reducing the risk of contamination.

In certain embodiments, the methods can be used to produce inocula that can be used for inoculating larger fermentation systems for scaled-up production.

Organisms that can be cultured using the subject invention can include, for example, yeasts, fungi, bacteria, archaea, protozoa and viruses. For example, production of inocula for cultivating *Starmerella* clade yeasts, *Pichia* clade yeasts, *Bacillus* clade bacteria, and any other species or strain of microorganism, can be achieved according to the methods of the subject invention.

In one embodiment, the subject invention provides inocula for generating microbe-based compositions, wherein an inoculum culture is produced from a purified, single-origin reference culture, which is divided into multiple standardized, high concentration aliquots. Advantageously, the inocula can be produced, stored, and then used as seed cultures for larger scale cultivation without need for producing a new culture with each intended use. This allows for consistency and repeatability when producing multiple larger scale cultures, either concurrently or serially; thus, practice of the subject invention can result in significant savings of time and cost. Furthermore, the end products produced from the inoculum can include viable microbes at the time of application in predictable, standardized concentrations.

Figure 1A:
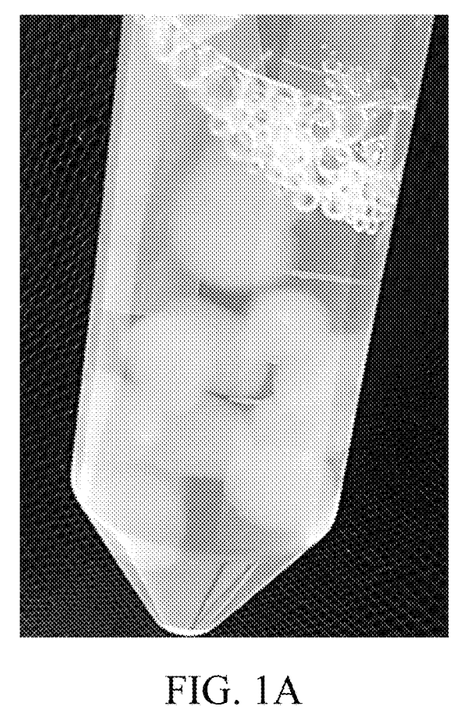
FIGS. 1A-1B show examples of inoculum pellets produced according to the subject invention. The inoculum pellets are shown being stored in tubes, which can be placed in a freezer for long-term preservation or a refrigerator for short-term storage and use.
Figure 1B:
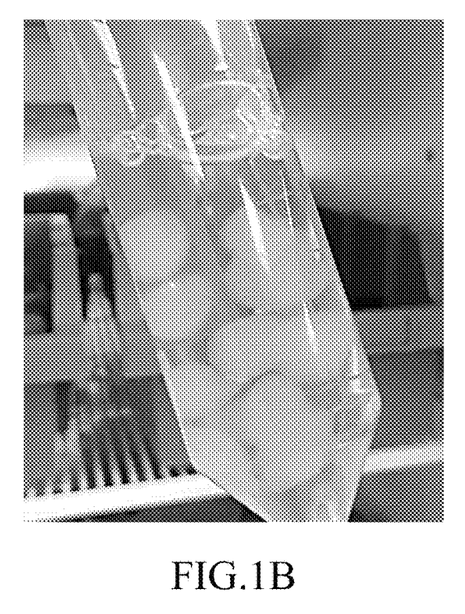

In preferred embodiments, the subject invention provides methods of producing multiple standardized, high concentration inocula comprising the steps of mixing alginate and agar to produce a semi-viscous solution; obtaining a purified reference culture of a microorganism; mixing the culture with the semi-viscous solution; depositing aliquots of the culture mixed with semi-viscous solution as droplets into a cold $CaCl_2$ solution; adding a sterilized cryoprotectant, such as glycerol, to the $CaCl_2$ solution; and placing the $CaCl_2$ solution having the culture, semi-viscous solution and glycerol therein, into a refrigerator at $-10°$ C. to $4°$ C., wherein each droplet of culture mixed with semi-viscous solution forms an individual pellet of high concentration inoculum. In one embodiment, the pellets may be round, as shown in FIGS. 1A-1B.

In one embodiment, the alginate and agar are heated prior to or concurrently with mixing. In one embodiment, the semi-viscous solution is autoclaved after mixing.

In one embodiment, the ratio of semi-viscous solution to culture is about 1:0.25.

In one embodiment, the glycerol is mixed with the $CaCl_2$ prior to depositing the aliquots into the $CaCl_2$.

Advantageously, the methods can be used to produce inocula having a high concentration of culture, meaning a concentration of hundreds, thousands, tens of thousands, hundreds of thousands or more cells, propagules and/or microorganisms per inoculum pellet. For example, one inoculum pellet can comprise $1\times10^3$, $1\times10^4$, $1\times10^5$, $1\times10^6$, $1\times10^7$, $1\times10^8$, $1\times10^9$, $1\times10^{10}$, or $1\times10^1$ or more, cells, propagules or microorganisms.

In a further embodiment, the subject methods comprise preserving the multiple identical, high concentration inocula in such a way that they can be readily accessed and used over long periods of time. Inoculum pellets can be placed in a freezer at temperatures between $-80°$ C. to $-10°$ C., for as long as necessary, while retaining the efficacy and viability of the microorganisms within the inoculum. For example, the inoculum pellets can be stored in tubes (such as those shown in FIGS. 1A-1B) or other sealable containers in the freezer, as long as 1 month, 6 months, or 1, 2, 3, 4, 5, or even 10 or more years, or longer.

In one embodiment, a method of inoculating a scaled-up microbial culture is provided wherein the inocula produced according to the subject invention are used. For example, when an inoculum culture is needed, a needle or other device suitable for handling small objects, such as fine point tweezers or an inoculating loop, can be used to transfer one or more inoculum pellets from the freezer where they are being stored and into a flask having, for example, fermentation broth therein. The inoculum can then be cultured to a desired concentration using, for example, a shaker or drum mixer. The inoculum pellet can be transferred directly from the freezer, or can be thawed in a refrigerator prior to being placed in a flask or other fermentation vessel for cultivation. Advantageously, only one pellet is needed at a time to be useful for inoculating a scaled-up cultivation operation.

Advantageously, the subject invention reduces the capital and labor costs of producing microorganisms and their metabolites. Furthermore, the cultivation process of the subject invention reduces or eliminates the need to concentrate or otherwise process microbes after completing scaled-up cultivation.

Compositions produced by the present invention can be used to inoculate large-scale fermentation systems for use in a wide variety of applications, including, for example, research laboratories, as well as the oil and gas industry, agriculture, human and animal health, food preservation, bioremediation, pharmaceuticals and cosmetics.

In one embodiment, the subject invention provides methods of producing a surfactant, solvent, enzyme, and/or other metabolite, by cultivating a microbe strain according to the methods of the subject invention under conditions appropriate for growth and metabolite production; and, optionally, purifying the metabolite.

The microbe-based products of the subject invention, including the high concentration inocula, can be used in a variety of unique settings because of, for example, the ability to efficiently deliver fresh fermentation broth with active biosurfactants or other metabolites; a mixture of cells, or other microbial propagules, and fermentation broth; a composition with a high density of vegetative cells, spores, conidia, mycelia and/or other viable microbial propagules; microbe-based products on short-order; and microbe-based products in remote locations.

DETAILED DESCRIPTION OF THE INVENTION

The present invention provides methods for producing and preserving microorganisms that can be used in research labs and in microbe-based compositions used in industries such as oil and gas, agriculture, bioremediation, aquaculture, human and animal health and many others. Specifically, the subject invention provides methods and materials for efficient cultivation of inocula for producing microorganisms and microbial growth by-products.

In specific embodiments, the subject invention provides simple, reliable methods of producing large quantities of standardized, high concentration inocula in solid form. Advantageously, the methods allow for production of inocula that can be preserved and stored for an extended period of time, for example a period of months or even several years or more.

Additionally, the inocula are relatively inexpensive to produce, and can significantly decrease the amount of work, money and time that must be spent producing cultures for research and/or other uses. The method can help prevent the culture from developing mutations over time, thus enabling genetically consistent culture for research and production. The inocula can also be shaped and sized to enable a user to conveniently and accurately transfer a specified amount of inoculating material, such as a specific number of cells, propagules or microorganisms, from one container to another, using standard laboratory equipment. Furthermore, the present invention can simplify production and facilitate consistent repetition of cultivation procedures, while also reducing the risk of contamination.

In certain embodiments, the methods can be used to produce inocula of any single-celled microorganism or a propagule thereof, which can be used for inoculating larger fermentation systems for scaled-up production.

In preferred embodiments, the methods of producing multiple standardized, high concentration inocula comprise the steps of mixing alginate and agar to produce a semi-viscous solution; obtaining a purified reference culture of a microorganism; mixing the culture with the semi-viscous solution; depositing aliquots of the culture mixed with semi-viscous solution as droplets into a cold $CaCl_2$ solution; adding a sterilized cryoprotectant, such as glycerol, to the $CaCl_2$ solution; and placing the $CaCl_2$ solution having the culture, semi-viscous solution and glycerol therein, into a refrigerator at −10° C. to 4° C., wherein each droplet of culture mixed with semi-viscous solution forms an individual pellet of high concentration inoculum. In one embodiment, the pellets may be round, as shown in FIGS. 1A-1B.

Compositions produced according to the present invention can be used to inoculate large-scale fermentation systems for use in a wide variety of, for example, petroleum industry applications. These applications include, but are not limited to, enhancement of crude oil recovery; reduction of oil viscosity; paraffin removal from rods, tubing, liners, and pumps; petroleum equipment corrosion prevention; fracturing fluids; reduction of $H_2S$ concentration in extracted crude oil; as well as tank, flowline and pipeline cleaning.

Other applications for the inocula produced according to the methods of the present invention include aquaculture, agriculture, horticulture, medicine, bioremediation, waste removal, human and animal health, food preservation, cosmetics and countless others.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with medium in which they were grown, in the microbe-based composition. The cells may be present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more propagules per milliliter of the composition. As used herein, a propagule is any portion or form of a microorganism from which a new and/or mature organism can develop, including but not limited to, cells, conidia, spores (including, e.g., reproductive spores, endospores and exospores), cysts, mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied.

The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain means is removed from the environment in which it exists in nature; thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, enzymes, toxins, acids, solvents, alcohols, proteins, vitamins, minerals, microelements, amino acids, polymers, and surfactants.

The term "inoculum" (plural "inocula") can be encompassed within the term "microbe-based product." As used herein, inoculum means a microbe-based product that can be used, for example, as a seed culture to inoculate a larger scale fermentation system or process. The inoculum can be scaled in such a fermentation system to produce desired quantities of microbe-based compositions and products. The inoculum according to one or more preferred embodiments of the present invention are defined by their rounded shape, allowing for convenient handling and transport between containers using standard laboratory equipment. The inocula of the present invention are preferably in a solid or semi-solid form, meaning they are neither liquid nor gaseous and do not flow under their own weight. Alternatively, the term "solid" when referring to an inoculum of the present invention means that the inoculum is sufficiently firm such that it maintains its rounded shape and can be conveniently handled using, for example, a needle, a pair of fine-point tweezers, or an inoculating loop.

As used herein, a "rounded" or "round" shape refers to a sphere, hemisphere, spheroid, and/or an ellipsoid shape, and/or any variation thereof, such as a cube with rounded corners/edges.

As used herein, "on-site fermentation system" refers to a system used for producing microbe-based compositions and/or products at or near to the site of application of these microbe-based compositions and/or products. The on-site fermentation system can be, for example, less than 1 mile, 2, 3, 4, 5, 6, 7, 8, 9, 10, 20, 50 or 100 miles away from the site of application, or any number of miles within this range.

As used herein, "harvested" refers to removing some or all of the microbe-based composition from a growth vessel.

As used herein, the term "plurality" refers to any number or amount greater than one.

As used herein, the term "probiotic" refers to microorganisms, which, when administered in adequate amounts, confer a health benefit on the host. The probiotics may be available in foods and dietary supplements (for example through capsules, tablets, and powders). Non-limiting examples of foods containing probiotics include dairy products such as yogurt, fermented and unfermented milk, smoothies, butter, cream, hummus, kombucha, salad dressing, miso, tempeh, nutrition bars, and some juices and soy beverages. In preferred embodiments, the microorganisms are live or in spore form.

By "reduces" is meant a negative alteration of at least 1%, 5%, 10%, 25%, 50%, 75%, or 100%.

By "reference" is meant a standard or control condition.

By "salt-tolerant" is meant capable of growing in a sodium chloride concentration of fifteen (15) percent or greater. In a specific embodiment, "salt-tolerant" refers to the ability to grow in 150 g/L or more of NaCl.

By "surfactant" is meant compounds that lower the surface tension (or interfacial tension) between two liquids or between a liquid and a solid. Surfactants act as detergents, wetting agents, emulsifiers, foaming agents, and dispersants. A "biosurfactant" is a surface-active substance produced by a living cell.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, or 20 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Cultivation of Purified Reference Culture and Growth Medium

In certain embodiments, the subject invention can be used to produce inocula of any type of single-celled microbial culture, which can be used to inoculate larger fermentation systems for scaled-up production. Thus, the subject invention provides methods for the efficient production of scalable cultures.

In preferred embodiments, the subject invention provides methods of producing multiple, standardized high concentration inocula from a purified, single-origin batch of reference culture. This reference culture can be cultivated using fermentation methods known in the art, for example, through cultivation processes ranging from small to large scale. The cultivation process can be, for example, submerged cultivation, solid state fermentation (SSF), and/or a combination thereof.

The microbe growth vessel used according to the subject invention can be any enclosed fermenter or cultivation reactor for laboratory or industrial use. In one embodiment, the fermenter can be a drum mixer or other standard vessel or laboratory mixing apparatus for growing culture.

The method can provide easy oxygenation of the growing culture with, for example, slow motion of air to remove low-oxygen containing air and introduction of oxygenated air. The oxygenated air may be ambient air supplemented periodically, such as daily.

In one embodiment, the vessel may optionally have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

The method and equipment for cultivation of microorganisms and production of the microbial by-products can be performed in a batch process or a quasi-continuous process.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the mixing device is a mobile or portable bioreactor that may be provided for on-site production of a liquid batch culture for producing inocula including a suitable amount of a desired strain of microorganism. The amount of liquid culture produced can be, for example, 2 to 500 liters, 5 to 250 liters, 10 to 100 liters, 15 to 75 liters, 20 to 50 liters, or 35 to 40 liters.

In one embodiment, total sterilization of equipment and substrate used in the subject cultivation methods is not necessary. However, the equipment and substrate can optionally be sterilized. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, air can pass through at least one filter before being introduced into the vessel. In other embodiments, the medium may be pasteurized or, optionally, no heat at all added, where the use of low water activity and low pH may be exploited to control bacterial growth.

The method can comprise adding one or more antimicrobial substances to prevent contamination during cultivation (e.g., streptomycin, oxytetracycline, sophorolipid, and rhamnolipid). Furthermore, the method can include pre-cultivation decontamination materials such as bleach and hydrogen peroxide. The bleach and hydrogen peroxide can come in concentrated form and later be diluted at the fermentation site before use. For example, the hydrogen peroxide can be provided in concentrated form and be diluted to formulate 1.0% to 3.0% hydrogen peroxide (by weight or volume). This can be done before or after a hot water rinse at, e.g., 80-90° C. to prevent contamination. The culture medium components (e.g., the carbon source, water, lipid source, micronutrients, etc.) can also be temperature decontaminated and/or hydrogen peroxide decontaminated (potentially followed by neutralizing the hydrogen peroxide using an acid such as HCl, $H_2SO_4$, etc.).

In some embodiments, one or more antimicrobial substances can be added to the culture medium (e.g., streptomycin, oxytetracycline, sophorolipid, and rhamnolipid) to further prevent contamination, before, during, or after fermentation.

Advantageously, the fermentation vessel can also be self-sterilizing. For example, microorganisms chosen for cultivation can be strains known to produce antimicrobial metabolites or byproducts, such as biosurfactants. Thus, the microbe culture itself can provide control of unwanted microorganisms inside the device, simultaneously with cultivation of the desired microorganisms.

Additionally, antifoaming agents may also be added to prevent the formation and/or accumulation of foam during cultivation and fermentation.

In one embodiment, the cultivation can be supplemented with one or more organic and inorganic nitrogen sources. The nitrogen source can be, for example, potassium nitrate, ammonium nitrate ammonium sulfate, ammonium phosphate, ammonia, urea, and/or ammonium chloride, as well as proteins, amino acids, yeast extracts, yeast autolysates, corn peptone, casein hydrolysate, and soybean protein. These nitrogen sources may be used independently or in a combination of two or more.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, coconut oil, canola oil, rice bran oil, olive oil, corn oil, sesame oil, and/or linseed oil; etc. Other carbon sources can include one or more sugars such as xylose, galactose, sorbose, ribose, arbutin, raffinose erythritol, xylitol, gluconate, citrate, molasses, hydrolyzed starch, corn syrup, and hydrolyzed cellulosic material including glucose. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included, e.g., L-Alanine.

The method can comprise adding one or more lipid sources such as, for example, oils or fats of plant or animal origin that contain free fatty acids or their salts or their esters, including triglycerides. Examples of fatty acids include, but are not limited to, free and esterified fatty acids containing from 16 to 18 carbon atoms, hydrophobic carbon sources, palm oil, animal fats, coconut oil, oleic acid, soybean oil, sunflower oil, canola oil, stearic and palmitic acid.

The method can comprise adding one or more micronutrient sources, such as potassium, magnesium, calcium, zinc and manganese, preferably as salts; phosphorous, such as from phosphates; and other growth stimulating components. In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate (e.g., ferrous sulfate heptahydrate), iron chloride, manganese sulfate, manganese sulfate monohydrate, manganese chloride, zinc sulfate, lead chloride, copper sulfate, calcium chloride, calcium carbonate, and/or sodium carbonate. These inorganic salts may be used independently or in a combination of two or more.

Each of the sources of nutrients can be provided in an individual package that can be added to the mixing apparatus at appropriate times during the cultivation process. Each of the packages can include several sub-packages that can be added at specific points (e.g., when culture, pH, and/or nutrient levels go above or below a specific concentration) or designated times (e.g., after 10 hours, 20 hours, 30 hours, 40 hours, etc.) during the cultivation process.

In one embodiment, the method for cultivation of microorganisms is carried out at about 5° to about 100° C., preferably, 15° to 60° C., more preferably, 20 to 50° C. or 25 to 40° C. In a further embodiment, the cultivation may be carried out continuously at a constant temperature. In another embodiment, the cultivation may be subject to changing temperatures.

A thermometer can be used to monitor temperature and the thermometer can be manual or automatic. An automatic thermometer can manage the heat and cooling sources appropriately to control the temperature throughout the cultivation process.

In one embodiment, the moisture level of the mixture should be suitable for the microorganism of interest. In a further embodiment, the moisture level may range from 20% to 90%, preferably, from 30 to 80%, more preferably, from 40 to 60%.

The pH of the mixture should be suitable for the microorganism of interest. Buffers, and pH regulators, such as carbonates and phosphates, may be used to stabilize pH near a preferred value. For example, the culture can be grown in a pH range from about 2 to 10 and, more specifically, at a pH range of from about 3 to 5 (by manually or automatically adjusting pH using bases, acids, and buffers; e.g., HCl, KOH, NaOH, $H_3PO_4$). The invention can also be practiced outside of this pH range.

Yeast cultivation, for example, can start at a first pH (e.g., a pH of 4.0 to 4.5) and later change to a second pH (e.g., a pH of 3.2-3.5) for the remainder of the process to help avoid contamination as well as to produce other desirable results (the first pH can be either higher or lower than the second pH).

Preferable results may be achieved by keeping the dissolved oxygen concentration above 10, 15, 20, or 25% of saturation during cultivation. Additionally, when metal ions are present in high concentrations, use of a chelating agent in the liquid medium may be necessary.

In preferred embodiments, the fermentation system operates continuously throughout the process of cultivation. The system can be operated for as long as necessary to produce a sufficient volume of culture, depending on the particular microbe species being produced. For example, the system can be run continuously for multiple days. In specific embodiments, the system is run continuously for 1, 2, 3, 4, or up to 5 days or more.

Methods of Producing High Concentration Inocula

The present invention provides methods for producing and preserving microorganisms and/or propagules thereof, as well as microbe-based compositions that can be used in the oil and gas industry, agriculture, bioremediation, aquaculture, and many other applications. Specifically, the subject invention provides methods and materials for efficient cultivation of inocula for producing scaled-up microorganism cultures and microbial growth by-products.

More specifically, the subject invention provides simple, reliable methods of producing large quantities of standardized, high concentration inocula in solid form. Advantageously, the methods allow for production of inocula that can be preserved and stored for an extended period of time, for example a period of months or even several years or more.

Additionally, the inocula are relatively inexpensive to produce, and can significantly decrease the amount of work, money and time that must be spent producing cultures for research and/or other uses. The inocula can also be shaped and sized to enable a user to conveniently and accurately transfer a specified amount of inoculating material, such as a specific number of cells, propagules or microorganisms, from one container to another, using standard laboratory equipment. Furthermore, the present invention can simplify production and facilitate consistent repetition of cultivation procedures, which can further help to reduce and/or eliminate the occurrence of genetic mutation and/or contamination within a culture sample over time.

In one embodiment, the subject invention provides inocula for generating microbe-based compositions, wherein an inoculum culture is produced from a purified, single-origin reference culture, which is divided into multiple standardized, high concentration aliquots. Advantageously, the inocula can be produced, stored, and then used as seed cultures for larger scale cultivation without need for producing a new culture with each intended use. This allows for consistency and repeatability when producing multiple larger scale cultures, either concurrently or serially; thus, practice of the subject invention can result in significant savings of time and cost. Furthermore, the end products produced from the inoculum can include viable microbes at the time of application in predictable, standardized concentrations and with predictable genomes.

In preferred embodiments, the subject invention provides methods of producing multiple standardized, high concentration inocula comprising the steps of mixing alginate and agar to produce a semi-viscous solution; obtaining a purified reference culture of a microorganism; mixing the culture with the semi-viscous solution; depositing aliquots of the culture mixed with semi-viscous solution as droplets into a cold $CaCl_2$ solution; adding a sterilized cryoprotectant, such as, for example, glycerol, to the $CaCl_2$ solution; and placing the $CaCl_2$ solution having the culture, semi-viscous solution and glycerol therein, into a refrigerator, wherein each droplet of culture mixed with semi-viscous solution forms an individual pellet of high concentration inoculum. In one embodiment, the pellets may be round, as shown in FIGS. 1A-1B.

In preferred embodiments, the refrigerator is set to a temperature of about −15° C. to about 4° C., or about −10° C. to about 4° C., or about −10° C. to about 0° C.

In one embodiment, the $CaCl_2$ solution having the culture, semi-viscous solution and glycerol therein can be placed directly into a freezer rather than being placed in the refrigerator. The freezer can be set to a temperature of, for example, about −80° C. to about 0° C., preferably from about −80° C. to about −10° C.

In one embodiment, the method is carried out in a clear plastic or glass container, such as, for example, a tube, flask, cylinder or dish, or other similar standard laboratory container.

A "high concentration" refers to, for example, at least $10^1$, $10^2$, $10^3$, $10^4$, $10^5$, $10^6$ or more cells or propagules (e.g., reproductive spores, endospores, exospores, cysts, buds, conidia, mycelia) of a desired single-celled microorganism per inoculum.

The term "standardized" can be interchanged with "identical" when used to describe the inocula of the present invention, and means having the same, or about the same, concentration of the same cells or microorganisms, as well as the same, or about the same, total volume per pellet. Furthermore, standardized can include that the cells of each inoculum comprises genetic uniformity, meaning few, if any mutations and/or introductions of contaminating microbes, have occurred between inocula.

In one embodiment, the concentration of culture when mixed with the semi-viscous solution, is mixed at ratio of 1:0.25 to 1:0.5 (solution to culture). Thus, standardized inoculum pellets having the same or about the same culture concentration can have a culture concentration between about 1.5% to 3.0% (w/v). It will be understood by the skilled artisan, however, that the number of cells or propagules in the inoculum may be higher or lower, depending on the desired use of the inoculum.

In one embodiment, the methods can comprise heating the alginate and agar prior to or concurrently with mixing. In one embodiment, the semi-viscous solution can be autoclaved after mixing.

The alginate can be used in a concentration of about 0.1 to about 2.0% (w/v), preferably about 0.5 to about 1.5% (w/v).

The agar can be used in a concentration of about 0.1 to about 2.0% (w/v), preferably about 0.5 to about 1.0% (w/v).

In certain embodiments, the $CaCl_2$ solution can be about a 1.0% to about a 5.0% solution, preferably about a 2% solution. In one embodiment, the glycerol can be mixed with the $CaCl_2$ solution prior to depositing the aliquots into the $CaCl_2$. Furthermore, in certain embodiments, the glycerol can be added at about 5% to about 25% (v/v), preferably about 10% to about 15% (v/v).

In preferred embodiment, prior to adding the droplets to the $CaCl_2$ and cryoprotectant, the $CaCl_2$ and, optionally, the cryoprotectant, can be cooled to a temperature close to frozen, e.g., about −15° C. to about 4° C., or about −10° C. to about 0° C.

In a specific embodiment, the method can comprise the steps of mixing 1.5% (w/v) alginate and 1% (w/v) agar to produce a semi-viscous solution; obtaining a purified reference culture of a microorganism; mixing the culture with the semi-viscous solution at ratio of 1:0.25 to 1:0.5 (solution to culture); depositing aliquots of the culture mixed with semi-viscous solution as droplets into a cold 2% (w/v) $CaCl_2$ solution; adding sterilized 15% (v/v) glycerol, to the $CaCl_2$ solution; and placing the $CaCl_2$ solution having the culture, semi-viscous solution and glycerol therein, into a refrigerator at about −10° C. to about 4° C., wherein each droplet of culture mixed with semi-viscous solution forms an individual pellet of high concentration inoculum.

In one embodiment, the volume of each aliquot deposited into the $CaCl_2$ and cryoprotectant is between about 10 µl and about 5 ml. For example, each aliquot can have a volume of about 10 µl to about 50 µl, and/or to about 100 µl, and/or to about 500 µl, and/or to about 1.0 ml, and/or to about 5.0 ml. Droplets can be deposited using, for example, pipettes of appropriate volume or other standard laboratory equipment.

Cryoprotectants are well-known antifreeze compounds that are capable of protecting cells and other biological tissue from damage due to freezing and ice formation. Many animal and plant species native to colder climate zones produce natural cryoprotectants to protect their bodies and cells. Isolated and synthetic cryoprotectants are also used in preservation of living materials for biological research and in food products.

Exemplary cryoprotectants useful according to the present invention include, but are not limited to, glycols such as ethylene glycol, propylene glycol, and glycerol, dimethyl sulfoxide (DMSO), trehalose, 2-Methyl-2,4-pentanediol (MPD), and sucrose. In preferred embodiments, the cryoprotectant is glycerol.

In another embodiment, the subject methods comprise the step of preserving and subsequently storing the standardized high concentration inocula so that they can be accessed and used over long periods of time, for example in a series of experiments. Inoculum pellets can be kept in the freezer at temperatures between about −80° C. to about −10° C., or about −80° C. to about −20° C., for as long as needed while retaining the efficacy and viability of the biological material within, for example, as long as 1 month, 6 months, or 1, 2, 3, 4, 5, or even 10 or more years.

Preferably, the inoculum pellets are stored in plastic or glass tubes, vials, dishes, flasks or other standard laboratory containers. Each container can contain, for example, from 1 to 50 pellets, depending on the size of the container.

When an inoculum culture is needed, a needle or other device suitable for handling small objects, such as fine point tweezers or an inoculating loop, is used to transfer one inoculum pellet from the freezer into a flask having nutrient medium therein, at which point the inoculum can be cultured to a desired concentration using, for example, a shaker, or the devices and methods described above. Advantageously, the present invention allows for user-friendly, sterile methods of inoculating scalable cultures.

The pellet can be used directly from the freezer, or can be thawed in a refrigerator (e.g., at about −10° C. to about 4° C.) prior to being placed in a flask for cultivation. Advantageously, only one pellet is needed at a time to be useful as a seed culture for inoculating a scaled up cultivation process.

In some embodiments, rather than cultivating a pellet in a flask, one or more inoculum pellets can be placed directly into a larger fermentation reactor for scaled up cultivation thereof. For example, the reactor can have a volume of about 1 L to about 5,000, or about 10 L to about 2,500 L, or about 100 L to about 1,500 L.

The pellet(s) can be transferred directly from the refrigerator after production, without additional freezing or storage, or they can be transferred directly from freezer storage. The number of inoculum pellets transferred into the fermentation reactor will depend upon the size of the reactor and/or the volume of fermentation medium that is contained in the reactor. For example, the number of pellets can range from 1 to about 5,000, or about 5 to about 1,000, or about 10 to about 500, or about 50 to about 100.

Advantageously, direct transfer of inoculum pellets into a scaled up fermentation reactor removes intermediate steps in the process of producing large volumes of microbe-based compositions, such as the flask growth step. Thus, the risks of genetic variability and contamination are significantly reduced, and the need for sampling and testing the culture to ensure genetic purity is obviated.

Advantageously, the subject invention reduces the capital and labor costs of producing microorganisms and their metabolites, due to the fact that, in one embodiment, the subject methods are capable of producing up to 100,000 or more inoculum pellets from one batch of reference culture. Furthermore, the cultivation process of the subject invention reduces or eliminates the need to concentrate microbes or otherwise test and/or process the microbes after completing scaled-up cultivation.

Types of Culture Grown According to the Present Invention

The culture grown according to the subject invention can be, for example, any organism that is capable of being grown in culture, other than tissue culture, including bacteria, archaea, yeast, fungi, viruses or protozoa. The microorganism can be in the form of vegetative cells or propagules, e.g., spores (including, e.g., reproductive spores, endospores and/or exospores), conidia, cysts, mycelia, buds, seeds, or combinations and/or variations thereof. Preferably, the microorganism is single-celled.

These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In one embodiment, the microorganism is a yeast or fungus. Yeast and fungus species suitable for use according to the current invention, include *Candida, Saccharomyces* (*S. cerevisiae, S. boulardii sequela, S. torula*), *Issatchenkia, Kluyveromyces, Pichia, Wickerhamomyces* (e.g., *W. anomalus*), *Starmerella* (e.g., *S. bombicola*), *Mycorrhiza, Mortierella, Phycomyces, Blakeslea, Thraustochytrium, Phythium, Entomophthora, Aureobasidium pullulans, Pseudozyma aphidis, Fusarium venenalum, Aspergillus, Trichoderma* (e.g., *T. reesei, T. harzianum, T. hamatum, T. viride*), *Rhizopus* spp., *Mycorrhiza* (e.g., *Glomus* spp., *Acaulospora* spp., vesicular-arbuscular mycorrhizae (VAM), arbuscular mycorrhizae (AM), endo- and ecto-mycorrhizae), entomopathogenic fungi (e.g., species of *Beauveria, Isaria, Hirsutella, Metarhizium* and *Nomuraea*), endophytic fungi (e.g., *Piriformis indica*), killer yeast strains, and combinations thereof.

In one embodiment, the microbe is a fungal or yeast strain capable of controlling pests, bioremediation, enhancing oil recovery and other useful purposes, e.g., *Starmerella bombicola, Candida* spp. (*C. apicola, C. batistae, C. floricola, C. riodocensis, C. stellate, C. kuoi, C.* sp. NRRL Y-27208), *Rhodotorula bogoriensis* sp., and *Wickerhamiella domericqiae*.

In one embodiment, the microbial strain is a sophorolipid-producing strain of the *Starmerella* clade. A culture of a *Starmerella* microbe that can be produced according to the subject invention, *Starmerella bombicola*, can be obtained from the American Type Culture Collection (ATCC), 10801 University Blvd., Manassas, Va. 20110-2209 USA. The deposit has been assigned accession number ATCC No. 22214 by the depository.

In one embodiment, the yeast is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. Such yeasts can include, but are not limited to, *Wickerhamomyces, Pichia* (e.g., *P. anomala, P. sydowiorum, P. guielliermondii, P. lynferdii, P. occidentalis, P. kudriavzevii*), *Hansenula, Saccharomyces, Hanseniaspora*, (e.g., *H. uvarum*), *Ustilago maydis, Debaryomyces hansenii, Candida, Cryptococcus, Kluyveromyces, Torulopsis, Ustilago, Williopsis, Zygosaccharomyces* (e.g., *Z. bailii*), and others.

In one embodiment, the microbe is a *Pichia* yeast selected from *Pichia anomala* (*Wickerhamomyces anomalus*), *Pichia guielliermondii, Pichia occidentalis* and *Pichia kudriavzevii. Pichia anomala*, in particular, is an effective producer of various solvents, enzymes, killer toxins, as well as sophorolipid biosurfactants.

In one embodiment, the microbe is a strain of *Pseudozyma aphidis*. This microbe is an effective producer of mannosylerythritol lipid biosurfactants.

In one embodiment, the microorganism is an archaea, or eubacteria, including, but not limited to, *Methanobacteria, Methanococci, Methanomicrobia, Methanopyri, Halobacteria, Halococci, Thermococci, Thermoplasmata, Thermoproelei, Psychrobacter, Arthrobacter, Halomonas, Pseudomonas, Hyphomonas, Sphingomonas, Archaeoglobi, Nanohaloarchaea*, extremophilic archaea, such as thermophiles, halophiles, acidophiles, and psychrophiles, and combinations thereof.

In one embodiment, the culture is a viral culture, including but not limited to adenovirus, cytomegalovirus, viruses of the herpes family, varicella zoster, influenza, rhinovirus, measles, mumps, enteroviruses, and the like.

In preferred embodiments, the microorganisms are bacteria, including gram-positive and gram-negative bacteria. The bacteria may be, for example *Bacillus* (e.g., *B. subtilis, B. licheniformis, B. firmus, B. laterosporus, B. megaterium, B. amyloliquifaciens* and/or *Bacillus coagulans* GBI-30 (BC30)), *Clostridium* (*C. butyricum, C. tyrobutyricum, C. acetobutyricum, Clostridium* NIPER 7, and *C. beijerinckii*), *Azobacter* (*A. vinelandii, A. chroococcum*), *Pseudomonas* (*P. chlororaphis* subsp. *aureofaciens* (Kluyver), *P. aeruginosa*), *Agrobacterium radiobacter, Azospirillumbrasiliensis, Rhizobium, Sphingomonas paucimobilis, Ralslonia eulropha*, and/or *Rhodospirillum rubrum*.

In one embodiment, the microbe is a non-pathogenic strain of *Pseudomonas*. Preferably, the strain is a producer of rhamnolipid biosurfactants.

In one embodiment, the microbe is a strain of *Bacillus*, e.g., *B. subtilis, B. licheniformis, B. firmus, B. laterosporus, B. megaterium, B. amyloliquifaciens* and/or *Bacillus coagulans* GBI-30 (BC30).

In one embodiment, microorganism is a strain of *B. subtilis*, such as, for example, *B. subtilis* var. *locuses* B1 or B2, which are effective producers of, for example, surfactin and other biosurfactants, as well as biopolymers. This specification incorporates by reference International Publication No. WO 2017/044953 A1 to the extent it is consistent with the teachings disclosed herein. In another embodiment, the microorganism is a strain of *Bacillus licheniformis*, which is an effective producer of biosurfactants as well as biopolymers, such as levan.

A culture of the *B. subtilis* B1 microbe has been deposited with the American Type Culture Collection (ATCC), 10801 University Blvd., Manassas, Va. 20110-2209 USA. The deposit has been assigned accession number ATCC No. PTA-123459 by the depository and was deposited on Aug. 30, 2016.

In certain embodiments, the present invention utilizes *Bacillus subtilis* strains with enhanced biosurfactant production compared to wild type *Bacillus subtilis* as well as compared to other microbes used in oil recovery. Such *Bacillus subtilis* have been termed members of the B series, including, but not limited to, B1, B2 and B3.

In certain embodiments, the *Bacillus subtilis* strains are salt tolerant. Salt tolerance can be with respect to any one or more of a variety of salts. For example, the salt can be a monovalent salt such as a sodium or potassium salt, e.g., NaCl or KCl, or a divalent salt such as a magnesium or calcium salt, e.g., $MgCl_2$ or $CaCl_2$, or a trivalent salt. Given geographic sites to be treated, zinc, bromium, iron, or lithium salts are present in the composition or site. In preferred embodiments, the bacteria described herein are tolerant to NaCl as well as others of the aforementioned salts and are, therefore, widely useful for oil recovery.

In preferred embodiments, such strains are characterized by enhanced biosurfactant production compared to wild type *Bacillus subtilis* strains. In certain embodiments, the *Bacillus subtilis* strains have increased biopolymer solvent and/or enzyme production.

In certain embodiments, the microbe used according to the subject invention is *Bacillus licheniformis. B. licheniformis* is a gram-positive, mesophilic bacterium, capable of anaerobic growth. It can survive in harsh environments, and at temperatures ranging from 10 to 55° C. or higher, with optimal growth temperature around 50° C.

*Bacillus licheniformis* is an effective producer of biosurfactants, as well as biopolymers, including, for example, levan.

In certain embodiments, the microbe is the probiotic *Bacillus coagulans* GBI-30 (BC30). BC30 has been shown to promote digestive health, aide in reducing inflammation, and in combination with HMB, regulate imbalances in lipid metabolism and the immune system.

BC30 is capable of surviving the acidity of the stomach, thus allowing it to reach the intestines. It contains a natural protective layer of proteins, which allows it to not only survive the harsh environment of the stomach, but also allows it to survive most manufacturing processes. Moreover, BC30 may also out-compete other harmful bacteria that cause infections or may have other deleterious effects. BC30 may delay the onset of symptoms and promote quicker recovery from infection and/or colitis caused by *Clostridium dificile*. It may also be helpful in replenishing beneficial bacteria in the intestines for individuals who have been prescribed antibiotics.

Other microbial strains including, for example, strains capable of accumulating significant amounts of, for example, glycolipid-biosurfactants, can be used in accordance with the subject invention. Other microbial by-products useful according to the present invention include mannoprotein, beta-glucan and other metabolites that have bio-emulsifying and surface/interfacial tension-reducing properties.

In one embodiment, a single type of microbe is grown in the fermentation reactor (e.g., a mixing apparatus as described herein). In alternative embodiments, multiple microbes, which can be grown together without deleterious effects on growth or the resulting product, can be grown together in a single vessel. There may be, for example, 2 to 3 or more different microbes grown at the same time.

Methods of Preparing Microbe-Based Products Using Inocula of the Subject Invention Compositions produced according to the present invention can be used to inoculate large-scale fermentation systems for use in a wide variety of applications, including, for example, laboratory research, as well as in industries such as the oil and gas industry, agriculture, human and animal health, bioremediation, food preservation, pharmaceuticals and cosmetics.

In one embodiment, a method of inoculating a scaled-up microbial culture is provided wherein the inocula produced according to the subject invention are used. For example, when an inoculum culture is needed, a needle or other device suitable for handling small objects, such as fine point tweezers or an inoculating loop, can be used to transfer one or more inoculum pellets from the freezer where they are being stored and into a flask with, for example, fermentation broth therein.

In one embodiment, when, for example, the inoculum pellet comprises bacterial spores, a germination enhancer can be added to the fermentation broth. Suitable germination enhancers include, for example, L-alanine, manganese, L-valine, L-tyrosine, and others.

The inoculum can then be cultured to a desired concentration using, for example, a shaker or drum mixer. The inoculum pellet can be transferred directly from the freezer, or can be thawed in a refrigerator prior to being placed in the flask for cultivation. Advantageously, only one pellet is needed at a time to be useful for inoculating a scaled-up cultivation operation.

The microbe-based products of the subject invention include products comprising the microbes and/or microbial growth by-products and optionally, the growth medium and/or additional ingredients such as, for example, water, carriers, adjuvants, nutrients, viscosity modifiers, and other active agents.

The microbe-based products of the subject invention may be, for example, microbial inoculants, biopesticides, nutrient sources, remediation agents, health products, and/or biosurfactants.

In one embodiment, the subject methods can further be used to produce a microbial growth by-product, such as, for example, a biosurfactant, solvent, enzyme, and/or other metabolite, by cultivating an inoculum of a microbe strain according to the methods of the subject invention under conditions appropriate for growth and metabolite production. In another embodiment, the method for producing microbial growth by-products may further comprise steps of concentrating and purifying the by-product of interest.

The subject invention further provides microbe-based products, as well as uses for these products to achieve beneficial results in many settings including, for example, improved bioremediation and mining; waste disposal and treatment; enhancing livestock and other animal health; and promoting plant health and productivity by applying one or more of the microbe-based products.

One microbe-based product of the subject invention is the inoculum pellets comprising the culture medium containing the microorganism and/or the microbial growth by-products produced by the microorganism and/or any residual nutrients. The product of cultivation may be used directly without extraction or purification. If desired, extraction and purification can be easily achieved using standard extraction methods or techniques known to those skilled in the art.

The microorganisms in the inoculum may be in an active or inactive form. Advantageously, in accordance with the subject invention, the inoculum may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages there-between.

In on embodiment, inoculum pellets, when prepared according to the subject methods, can be packaged for storage. Each pellet contained in such a package can provide a stable, quantitative inoculum containing a standardized, i.e. substantially identical, predictable concentration of inoculating material. In some embodiment, one package can comprise from 1 to 50 or more pellets.

The subject invention further provides materials and methods for the production of biomass (e.g., viable cellular material), extracellular metabolites and solvents (e.g., both small and large molecules), and/or intracellular components (e.g., enzymes and other proteins). The microbes and microbial growth by-products of the subject invention can also be used for the transformation of a substrate, such as an ore, wherein the transformed substrate is the product.

In one embodiment, the subject invention provides a method of improving plant health and/or increasing crop yield by scaling the microbe-based product disclosed herein, for example in an on-site fermentation system, and applying the scaled product to soil, seed, or plant parts. In another embodiment, the subject invention provides a method of increasing crop or plant yield comprising multiple applications of the scaled product.

In one embodiment, the subject invention provides methods of producing a surfactant, solvent, enzyme, and/or other useful metabolite, by cultivating a microbe strain of the subject invention under conditions appropriate for growth and such metabolite production; and, optionally, at least to some extent, the metabolite. The microorganisms can grow in situ and produce the metabolites onsite. Consequently, a high concentration of metabolites and biosurfactant-producing microorganisms at a treatment site (e.g., an oil well) can be achieved efficiently and continuously.

In one embodiment, the composition is suitable for agriculture. For example, the composition can be scaled and used to treat soil, plants, and seeds. The composition may also be used as a pesticide.

In one embodiment, the subject invention further provides customizations to the materials and methods according to the local needs. For example, the method for cultivation of microorganisms may be used to grow those microorganisms located in the local soil or at a specific oil well or site of pollution. In specific embodiments, local soils may be used as the solid substrates in the cultivation method for providing a native growth environment. Advantageously, these microorganisms can be beneficial and more adaptable to local needs.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Production of *Starmerella* Reference Culture

A portable and distributable mixing device was used to produce *Starmerella bombicola* yeast as a reference culture using submerged cultivation. The mixing device had a working volume of 100 liters (L).

The culture medium used for producing the yeast inoculum comprised the components shown in Table 1.

TABLE 1

Components for reference culture medium.

| Reagent | Weight (g/L) |
| --- | --- |
| Yeast Extract | 5 |
| Glucose | 20 |
| Monopotassium phosphate | 2 |
| Dipostassium phosphate | 2 |
| Magnesium sulfate | 0.5 |

The culture medium components were sterilized in 1 L of 10% hydrogen peroxide overnight. The sterile composition was then mixed with filtered water in the fermentation vessel.

The cultivation temperature was generally about room temperature, from 18 to 250 Celsius. The initial pH of the medium was from about 5.5-6.0.

Under these cultivation conditions, industrially useful production of biomass, sophorolipids and other metabolites are achieved after about 1 to about 5 days of cultivation, preferably after a cultivation time of about 48 hours.

Upon completion of the cultivation, the final concentration of yeasts achieved is approximately 200 to 400 CFUs/ml. The culture can then be purified and used as a reference culture to produce the inoculum pellets of the subject invention.

Example 2—Inoculum Pellet Production

To produce the inoculum pellets according to the subject invention, 1.5% alginate and 1% agar solution was heated, mixed and autoclaved. The result was a semi-viscous solution. The semi-viscous solution was mixed with cultivated culture (e.g., the culture produced as described in Example 1) in a ratio of 1:0.25, solution:culture.

After mixing, drops of the mixture were added to pre-cooled 2% $CaCl_2$ solution using a standard laboratory pipetting apparatus. Then, 15% glycerol was added and the final mixture was put into a refrigerator at −10° C. to 4° C. The resulting pellets being stored in a standard plastic conical tube are shown in FIGS. 1A-1B. The container can be placed into a freezer and stored for extended periods of time. When needed, a pellet can be taken from its container and placed into prepared nutrient medium as an inoculum.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A method of producing standardized high concentration inocula comprising:
   obtaining a first composition by mixing alginate and agar;
   obtaining a purified reference culture of a microorganism;
   mixing the reference culture with the first composition to form a second composition;
   depositing aliquots of the second composition as droplets directly into a $CaCl_2$ solution that has a temperature of −15° C. to 4° C.;
   adding a sterilized cryoprotectant to the $CaCl_2$ solution; and
   placing the $CaCl_2$ solution having the second composition and the cryoprotectant therein, into a refrigerator at −10° C. to 4° C., wherein each droplet forms an individual inoculum pellet,
   removing the individual inoculum pellets from the refrigerator and placing them directly into a freezer for storage at a temperature between −80° C. and −10° C.,
   after storage, transferring one or more of the inoculum pellets directly from the freezer into a fermentation reactor having liquid fermentation broth therein, and cultivating the one or more inoculum pellets.

2. The method of claim 1, wherein the reference culture comprises a bacteria, yeast, fungi, archaea, virus, protozoan or propagules thereof.

3. The method of claim 2, wherein the propagules are vegetative cells, reproductive spores, endospores or exospores.

4. The method of claim 2, wherein the reference culture comprises one or more yeasts and/or fungi selected from *Starmerella*, *Pichia*, and *Mycorrhiza*.

5. The method of claim 2, wherein the reference culture comprises a *Bacillus* bacteria selected from *B. subtilis, B. licheniformis, B. firmus, B. laterosporus, B. megaterium, B. amyloliquefaciens* and *Bacillus coagulans* GBI-30 (BC30).

6. The method of claim 1, carried out in a plastic or glass container selected from a tube, flask, cylinder and dish.

7. The method of claim 1, wherein each inoculum pellet comprises $1 \times 10^1$ to $1 \times 10^6$ cells or propagules of the microorganism.

8. The method of claim 1, wherein the cryoprotectant is glycerol.

9. The method of claim 1, wherein the alginate and agar are heated prior to or concurrently with mixing.

10. The method of claim 1, wherein the cryoprotectant is mixed with the $CaCl_2$ prior to depositing the aliquots into the $CaCl_2$.

11. The method of claim 1, wherein each inoculum pellet has a volume that is between 10 μL and 5 ml.

12. The method of claim 1, wherein the fermentation broth comprises a germination enhancer.

13. A method of producing standardized high concentration inocula comprising:

obtaining a first composition by mixing 1.5% (w/v) alginate and 1% (w/v) agar;

heating the alginate and agar prior to or concurrently with mixing;

obtaining a purified reference culture of a microorganism;

mixing the reference culture with the first composition at a ratio of 1:0.5 (first composition to culture) to produce a second composition;

depositing aliquots of the second composition as droplets directly into a 2% (w/v) $CaCl_2$ solution that has a temperature of −15° C. to 4° C.;

adding sterilized 5-25% (v/v) glycerol to the $CaCl_2$ solution; and placing the $CaCl_2$ solution having the second composition and glycerol therein, into a refrigerator at −15° C. to 4° C., wherein each droplet forms an individual inoculum pellet, removing the individual inoculum pellets from the refrigerator and placing them directly into a freezer for storage at a temperature between −80° C. and −10° C., after storage, transferring one or more inoculum pellets directly from the freezer into a fermentation reactor containing liquid fermentation broth, wherein the fermentation reactor has a volume of 1 L to 5,000 L, and cultivating the one or more inoculum pellets.

* * * * *